(12) United States Patent
Deininger et al.

(10) Patent No.: US 11,575,236 B2
(45) Date of Patent: Feb. 7, 2023

(54) IMPLANTABLE PULSE GENERATOR CARRIER USED TO INTERFACE WITH MULTIPLE LEAD SIZES

(71) Applicant: Medtronic, Inc., Minneapolis, MN (US)

(72) Inventors: Steven Deininger, Plymouth, MN (US); Paul Eichstaedt, Blaine, MN (US); Randy S. Roles, Elk River, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 16/948,859

(22) Filed: Oct. 2, 2020

(65) Prior Publication Data

US 2021/0104853 A1 Apr. 8, 2021

Related U.S. Application Data

(60) Provisional application No. 62/915,887, filed on Oct. 16, 2019, provisional application No. 62/910,566, filed on Oct. 4, 2019.

(51) Int. Cl.
*H01R 31/06* (2006.01)
*A61N 1/36* (2006.01)
*A61N 1/375* (2006.01)

(52) U.S. Cl.
CPC ......... *H01R 31/06* (2013.01); *A61N 1/36125* (2013.01); *A61N 1/3752* (2013.01); *H01R 2201/12* (2013.01)

(58) Field of Classification Search
CPC .. H01R 13/639; H01R 31/06; H01R 2201/12; A61N 1/36125; A61N 1/3752
USPC ........................................................ 439/628
See application file for complete search history.

(56) References Cited

U.S. PATENT DOCUMENTS

| | | | |
|---|---|---|---|
| 4,583,543 A | | 4/1986 | Peers-Trevarton |
| 4,898,173 A | * | 2/1990 | Daglow ................ H01R 24/58 439/585 |
| 4,934,366 A | * | 6/1990 | Truex ................... A61N 1/3752 607/37 |
| 5,000,177 A | | 3/1991 | Hoffmann et al. |
| 5,413,595 A | * | 5/1995 | Stutz, Jr. .............. A61N 1/3752 607/37 |

(Continued)

OTHER PUBLICATIONS

"Precision™ M8 Adapter Directions for Use", Boston Scientific Corporation, Jul. 2015.

(Continued)

*Primary Examiner* — Abdullah A Riyami
*Assistant Examiner* — Vladimir Imas
(74) *Attorney, Agent, or Firm* — Patterson Thuente IP

(57) ABSTRACT

An apparatus and method of electrically coupling a previously implanted stimulation lead with a replacement neurostimulator device. The apparatus and method configured to operably couple a proximal portion of a neuromodulation adapter including a plurality of electrical conductors spaced apart at a first pitch spacing to a corresponding plurality of electrical terminals of a replacement neurostimulator device, and operably couple a distal end of the neuromodulation adapter including a plurality of conductor elements and an electrically active set screw spaced part of a second pitch spacing to a corresponding plurality of electrical connectors of a previously implanted stimulation lead.

14 Claims, 11 Drawing Sheets

(56) References Cited

U.S. PATENT DOCUMENTS

| | | | |
|---|---|---|---|
| 5,669,790 A * | 9/1997 | Carson | A61N 1/056 439/948 |
| 5,843,141 A * | 12/1998 | Bischoff | H01R 13/5224 607/37 |
| 6,205,358 B1 * | 3/2001 | Haeg | A61N 1/37512 29/857 |
| 7,083,474 B1 * | 8/2006 | Fleck | H01R 13/5804 439/669 |
| 7,526,339 B2 | 4/2009 | Lahti et al. | |
| 7,590,451 B2 * | 9/2009 | Tronnes | A61N 1/3752 607/37 |
| 7,736,192 B2 | 6/2010 | Alexander et al. | |
| 7,860,568 B2 | 12/2010 | Deininger et al. | |
| 7,881,783 B2 | 2/2011 | Bonde et al. | |
| 8,123,567 B2 * | 2/2012 | Kast | A61N 1/3752 439/857 |
| 8,140,163 B1 * | 3/2012 | Daglow | H01R 13/193 607/36 |
| 8,180,461 B2 | 5/2012 | Mamo et al. | |
| 8,251,731 B2 * | 8/2012 | Boyd | A61N 1/3752 439/281 |
| 8,401,649 B2 * | 3/2013 | Tronnes | A61N 1/3752 607/38 |
| 8,525,027 B2 | 9/2013 | Lindner et al. | |
| 8,831,744 B2 * | 9/2014 | Swanson | A61N 1/05 607/116 |
| 9,227,052 B2 * | 1/2016 | Robnett | A61N 1/05 |
| 9,427,574 B2 | 8/2016 | Lee et al. | |
| 9,472,916 B2 | 10/2016 | Hanson et al. | |
| 9,802,038 B2 * | 10/2017 | Lee | B23K 26/38 |
| 9,855,423 B2 | 1/2018 | Jiang et al. | |
| 10,905,871 B2 * | 2/2021 | Nageri | H01R 13/641 |
| 2003/0073348 A1 * | 4/2003 | Ries | A61N 1/3752 439/578 |
| 2003/0163171 A1 * | 8/2003 | Kast | H01R 24/58 607/36 |
| 2004/0176831 A1 | 9/2004 | Gliner et al. | |
| 2008/0183236 A1 | 7/2008 | Gerber | |
| 2012/0130438 A1 | 5/2012 | Seeley et al. | |
| 2012/0203292 A1 | 8/2012 | Deininger et al. | |
| 2014/0121741 A1 | 5/2014 | Bennett et al. | |
| 2018/0078760 A1 | 3/2018 | Lee et al. | |
| 2018/0175566 A1 | 6/2018 | Hanson et al. | |
| 2019/0190215 A1 | 6/2019 | Hanson et al. | |
| 2019/0336752 A1 | 11/2019 | Bauer et al. | |
| 2019/0374776 A1 | 12/2019 | Mishra et al. | |
| 2020/0398057 A1 | 12/2020 | Esteller et al. | |

OTHER PUBLICATIONS

"Precision™ S8 Adapter Directions for Use", Boston Scientific Corporation, Jun. 2018.

Matzel et al., "Sacral Neuromodulation: Standardized Electrode Placement Technique", Neuromodulation: Technology at the Neural Interface, vol. 20, Issue 8, Jun. 12, 2017, pp. 816-824.

Spinelli et al., "Evolution of a minimally-invasive procedure for sacral neuromodulation", Chapter 18: Development of Minimally-invasive SNS, New Perspectives in Sacral Nerve Stimulation, Martin Dunitz Ltd., Mar. 28, 2002, pp. 217-222.

Axonics Modulation Technologies, "Axonics Prepares for Introduction of its Sacral Neuromodulation System", as featured in Business in Focus, Mar. 2018, a Focus Media Group Publication.

Blok et al., "Programming settings and recharge interval in a prospective study of a rechargeable sacral neuromodulation system for the treatment of overactive bladder", Neurourology and Urodynamics, vol. 37, Issue 52, Oct. 20, 2017, pp. 1-6.

Cohn et al., "Evaluation of the axonics modulation technologies sacral neuromodulation system for the treatment of urinary and fecal dysfunction", Expert Review of Medical Devices, vol. 14, No. 1, Dec. 4, 2016, pp. 3-14.

Elterman, "The novel Axonics® rechargeable sacral neuromodulation system: Procedural and technical impressions from an initial North American experience", Neurourology and Urodynamics, vol. 37, Issue S2, Dec. 19, 2017, pp. 1-8.

U.S. Appl. No. 16/948,857, filed Oct. 2, 2020, Inventor(s): Formosa et al.

U.S. Appl. No. 16/948,856, filed Oct. 2, 2020, Inventor(s): Sandgren et al.

Application and file history for U.S. Appl. No. 17/249,555, filed Mar. 4, 2021, inventors Sell et al.

* cited by examiner

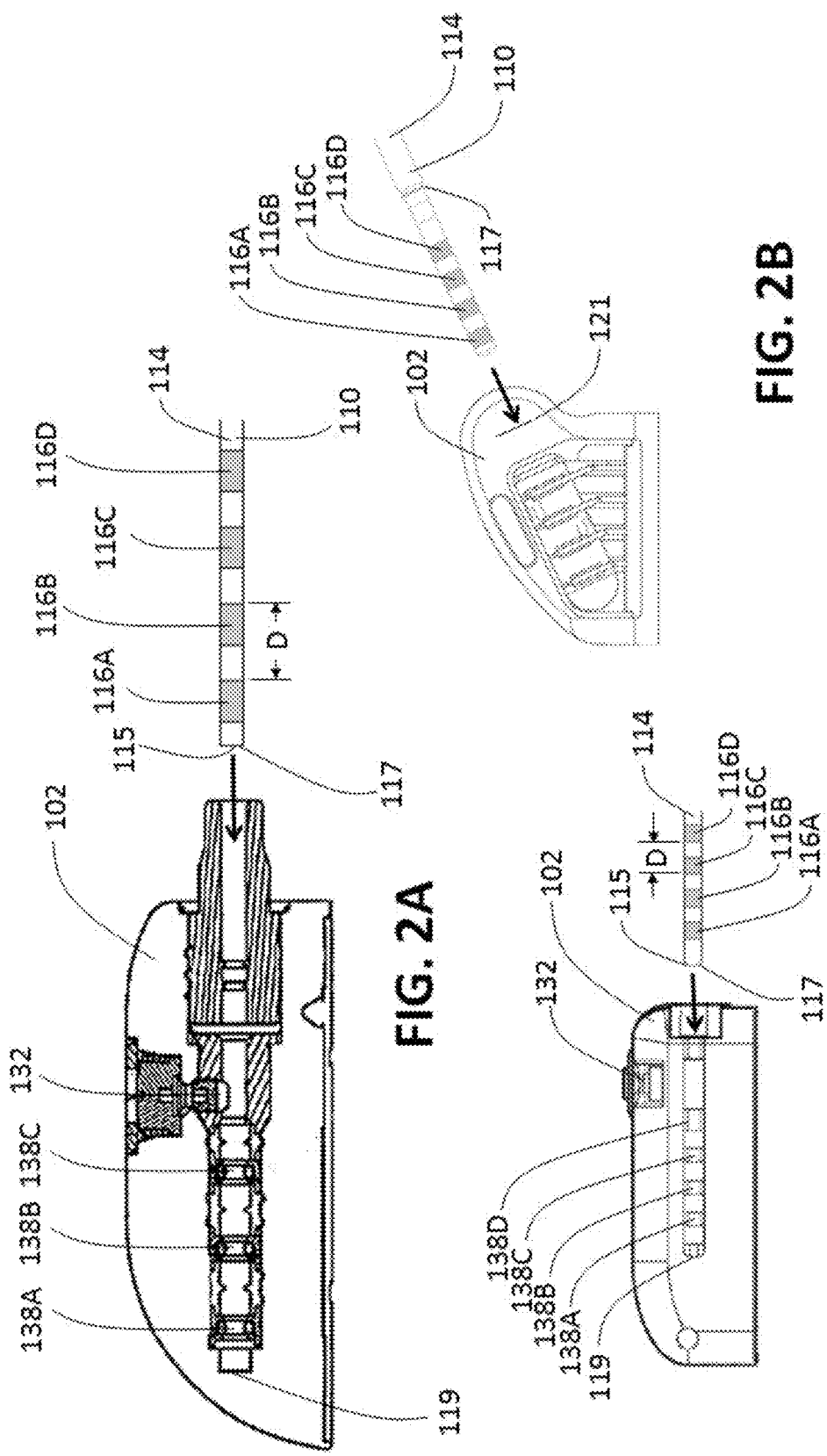

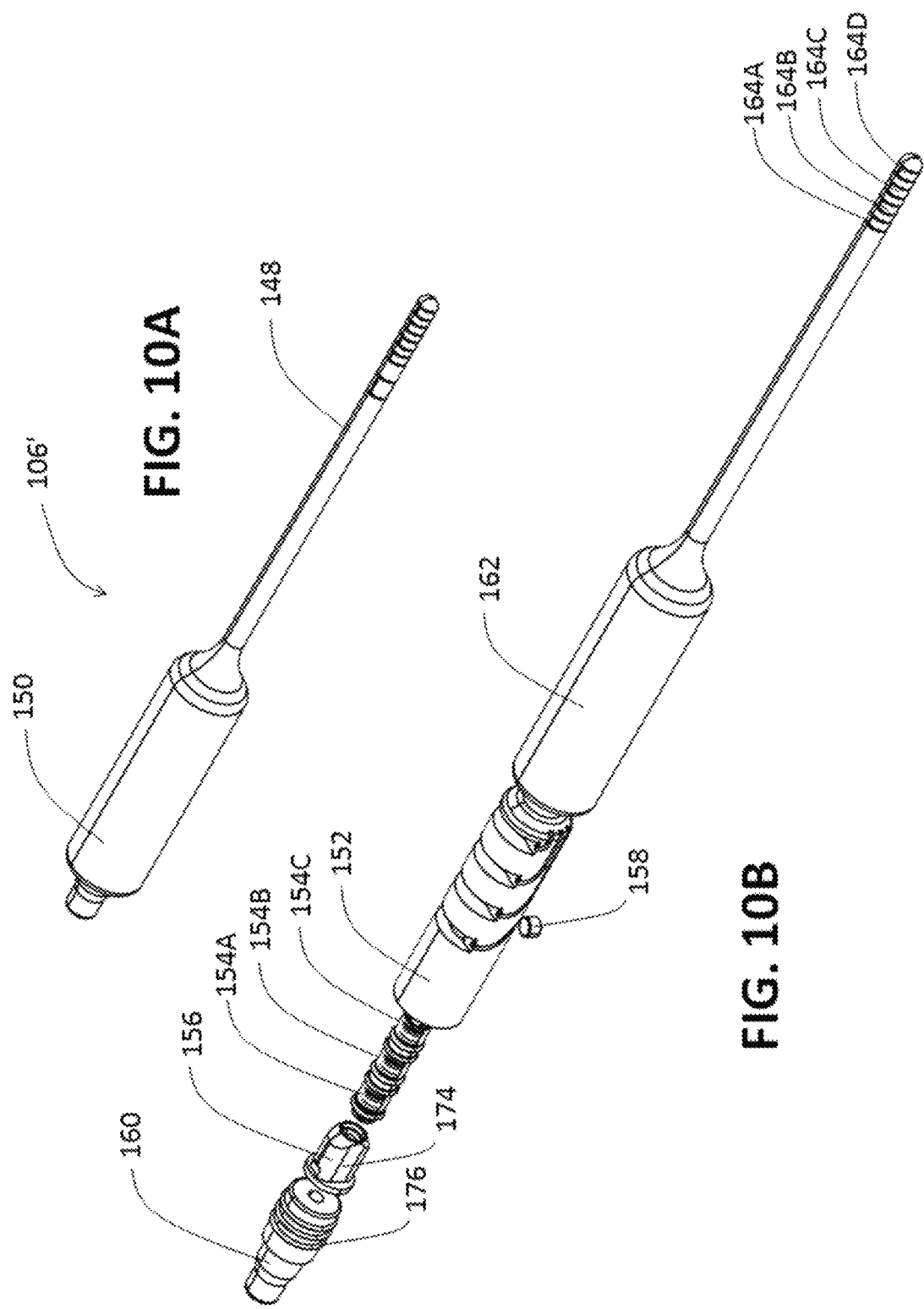

IMPLANTABLE PULSE GENERATOR CARRIER USED TO INTERFACE WITH MULTIPLE LEAD SIZES

CROSS-REFERENCE TO RELATED APPLICATIONS

The present application claims the benefit of U.S. Provisional Application No. 62/910,566, filed Oct. 4, 2019 and U.S. Provisional Application No. 62/915,887, filed Oct. 16, 2019, the disclosures of which are hereby incorporated by reference in their entireties.

FIELD

The present technology is generally related to methods, systems and devices related to electrical stimulation therapy.

BACKGROUND

A number of human bodily functions are affected by the nervous system. For example, bodily disorders, such as urinary incontinence, urinary urge/frequency, urinary retention, pelvic pain, bowel dysfunction (constipation, diarrhea, etc.), erectile dysfunction, etc. are all bodily functions influenced by the sacral nerves. One technique to treat such bodily disorders is sacral nerve stimulation therapy. Sacral nerve stimulation therapy is a treatment that uses a small device to send mild electrical impulses to nerves located in the lower region of the spine (just above the tailbone). These nerves, referred to as sacral nerves (specifically S2, S3 and S4), influence the behavior of structures such as the bladder, sphincter and pelvic floor muscles. In some cases, electrical stimulation of the sacral nerves can successfully eliminate or reduce the above mentioned bodily disorders.

Generally, implantation of a sacral neuromodulation system involves surgically implanting a stimulation lead near the sacral nerves. The stimulation lead is a small, insulated, electrical conductor with stimulation electrodes on the distal end for implementation near the sacral nerves, and an electrical connector on the proximal end of the lead. The proximal end electrical connector is typically connected to an implantable neurostimulator device that operates in a fashion broadly similar to that of a cardiac pacemaker by delivering occasional mild electrical pulses to the sacral nerve of the patient.

The power used to generate the mild electrical pulses typically originates from a primary cell or battery located in the implantable neurostimulator device. Over an extended period of use, the battery can become depleted. For example, some currently available implantable neurostimulator devices may have a battery lifetime of between about three to five years. Once the battery is depleted, it is common for patients to have the neurostimulator device replaced.

The emergence of implantable neurostimulator devices with rechargeable batteries has reduced the form factor of such devices. A rechargeable battery may be configured to last only a period of weeks between charges, and thus may be physically smaller in size than a battery intended to last years. As a result of this reduced size, the design of the stimulation leads compatible with newer devices has also changed. In particular, the size or configuration of the electrical connector on the proximal end of the lead has been reduced in size for improved mating with the smaller neurostimulator devices. As a result, some legacy and current stimulation leads may not be compatible with emerging and/or next-generation neuromodulation devices.

By contrast to the neurostimulator device, the stimulation leads typically have a much longer usable lifetime than the neurostimulator device. Further, replacement of the stimulation lead is typically considered a more invasive procedure, as unlike the neurostimulator device which is generally located just beneath the skin of the patient, the stimulation leads extend much further into the patient and are considered to be more challenging to place correctly. Additionally, many leads include one or more tines or barbs positioned on the distal end of the lead, which serve to anchor the lead in place within the patient as tissue fills in around the lead over time. Accordingly, it is generally considered preferable to leave the stimulation lead in place when the neurostimulator device is replaced. Unfortunately, not all stimulation leads are compatible with all neurostimulator devices. The present disclosure addresses this concern.

SUMMARY

The techniques of this disclosure generally relate to a neuromodulation adapter configured to enable an electrically compatible connection between otherwise incompatible leads and neurostimulation devices, for example between a previously implanted stimulation lead and a replacement neurostimulator device, so as to increase physician or patient options in replacing components of a neuromodulation system. A number of factors may cause incompatibility between an implantable stimulation lead and a neurostimulator device, such as variation in the number of electrodes (e.g., one, two, four, etc.) included on the lead, the spacing of electrical contacts on the lead in the region where the lead is connected to the neurostimulator device, diameter of the lead, use of active or inactive set screws, for example.

One embodiment of the present disclosure provides a neuromodulation adapter. The neuromodulation adapter can include a proximal portion and a distal portion. The proximal portion can include a plurality of electrical conductors spaced apart at a first pitch spacing and configured to electrically engage with the corresponding plurality of electrical terminals of a neurostimulator device. The distal portion can include a plurality of conductor elements and an electrically active set screw, the plurality of conductor elements and electrically active set screw can be spaced apart at a second pitch spacing and can be configured to electrically engage with a corresponding plurality of electrical connectors of a stimulation lead, wherein the first pitch spacing is different from the second pitch spacing.

In one embodiment, the proximal portion can include a datum reference configured to serve as a reference point for spacing of the plurality of electrical conductors relative to a corresponding plurality of electrical terminals of a neurostimulator device. In one embodiment, the distal portion can include at least one forward stop or abutting surface configured to serve as a reference point for spacing of the plurality of conductor elements relative to a corresponding plurality of electrical connectors of a stimulation lead. In one embodiment, the first pitch spacing can have a pitch of at least one of about 0.085 inches or about 2 mm. In one embodiment, the second pitch spacing can have a pitch of about 0.170 inches. In one embodiment, the neuromodulation adapter can further include a flexible portion located between the proximal portion and the distal portion configured to enable bending of the neuromodulation adapter to aid in an ideal positioning of a neurostimulator device relative to a stimulation lead within a body of a patient.

Another embodiment of the present disclosure can provide a method of electrically coupling a previously implanted stimulation lead with a replacement neurostimulator device. The method can include operably coupling a proximal portion of a neuromodulation adapter including a plurality of electrical conductors spaced apart at a first pitch spacing to a corresponding plurality of electrical terminals of a replacement neurostimulator device; and operably coupling a distal end of the neuromodulation adapter including a plurality of conductor elements and an electrically active set screw spaced apart at a second pitch spacing to a corresponding plurality of electrical connectors of a previously implanted stimulation lead.

Another embodiment of the present disclosure can provide a neuromodulation adapter configured to provide electrical coupling between a stimulation lead having a pitch spacing of about 0.170 inches and a neurostimulator device having a pitch spacing of at least one of about 0.085 inches or about 2 mm. The neurostimulator adapter can include a proximal portion and a distal portion. The proximal portion can include a plurality of electrical conductors spaced apart at a first pitch spacing of at least one of about 0.085 inches or about 2 mm and can be configured to electrically engage with a corresponding plurality of electrical terminals of a neurostimulator device, wherein the proximal portion further includes a datum reference configured to serve as a reference point for spacing of the plurality of electrical conductors relative to a corresponding plurality of electrical terminals of a neurostimulator device. The distal portion can include a plurality of conductor elements and an electrically active set screw, the plurality of conductor elements and electrically active set screw can be spaced apart at a second pitch spacing of about 0.170 inches and can be configured to electrically engage with the corresponding plurality of electrical connectors of a stimulation lead, wherein the distal portion further includes at least one forward stop or abutting surface configured to serve as a reference point for spacing of the plurality of conductor elements relative to a corresponding plurality of electrical conductors of a stimulation lead.

Another embodiment of the present disclosure provides a neuromodulation adapter having a housing defining a first cavity shaped and sized to receive at least a portion of an implantable neurostimulator device therein, a second cavity shaped and sized to receive a proximal end portion of a stimulation lead, and a plurality of electrical conductors configured to contact a plurality of electrical terminals of an implantable neurostimulator device received within the first cavity, the plurality of electrical conductors in electrical communication with a corresponding plurality of connector elements configured to contact a plurality of electrical connectors of a proximal end of a stimulation lead received within the second cavity, thereby enabling an electrical compatible connection between a previously implanted stimulation lead and a replacement neurostimulator device.

Another embodiment of the present disclosure provides a method of electrically coupling a previously implanted stimulation lead with a replacement neurostimulator device, comprising: positioning at least a portion of a replacement neurostimulator device within a first cavity defined within a housing of a neuromodulation adapter, wherein the housing includes a plurality of electrical conductors configured to contact a plurality of electrical terminals of the replacement neurostimulator device; and positioning a proximal end portion of a previously implanted stimulation lead within a second cavity defined within the housing of the neuromodulation adapter, wherein the housing includes a plurality of conductor elements configured to contact the plurality of electrical connectors at the previously implanted stimulation lead, wherein the plurality of electrical conductors are in electrical communication with a plurality of connector elements, thereby enabling an electrical compatible connection between the previously implanted stimulation lead and replacement neurostimulator device.

Yet another embodiment of the present disclosure provides a neuromodulation adapter configured to enable an electrically compatible connection between a previously implanted stimulation lead and a replacement neurostimulator device. The neuromodulation adapter can include a housing defining a first cavity shaped and sized to receive at least a portion of a replacement neurostimulator device therein, a second cavity shaped and sized to receive a proximal end portion of a previously implanted stimulation lead, where in an exterior of the housing is shaped and sized to generally mimic the shape and size of a previously implanted neurostimulator device. The neuromodulation adapter can further include a plurality of electrical conductors configured to contact a plurality of electrical terminals of the replacement neurostimulator device received within the first cavity, the plurality of electrical conductors in electrical communication with a plurality of connector elements configured to contact a plurality of electrical connectors of a proximal end of the previously implanted stimulation lead received within the second cavity, wherein the plurality of connector elements are spaced apart from one another at a pitch of approximately 0.170 inches. The neuromodulation adapter can further include a set screw configured to enable a proximal end of the previously implanted stimulation lead received within the second cavity to be secured in position relative to the housing.

The details of one or more aspects of the disclosure are set forth in the accompanying drawings and the description below. Other features, objects, and advantages of the techniques described in this disclosure will be apparent from the description in the drawings, and from the claims.

BRIEF DESCRIPTION OF DRAWINGS

The disclosure can be more completely understood in consideration of the following detailed description of various embodiments of the disclosure, in connection with the accompanying drawings, in which:

FIG. 2A is a cross-sectional profile view depicting a proximal portion of a stimulation lead and a neurostimulator device, in accordance with a first embodiment of the disclosure.

FIG. 2B is a cross-sectional profile view depicting a proximal portion of a stimulation lead and a neurostimulator device, in accordance with a second embodiment of the disclosure.

FIG. 2C is a cross-sectional profile view depicting a proximal portion of a stimulation lead and a neurostimulator device, in accordance with a third embodiment of the disclosure.

FIG. 10A is a perspective view depicting a neuromodulation adapter, in accordance with an embodiment of the disclosure.

FIG. 10B is an exploded, perspective view depicting the neuromodulation adapter of FIG. 10A.

Figure 1:
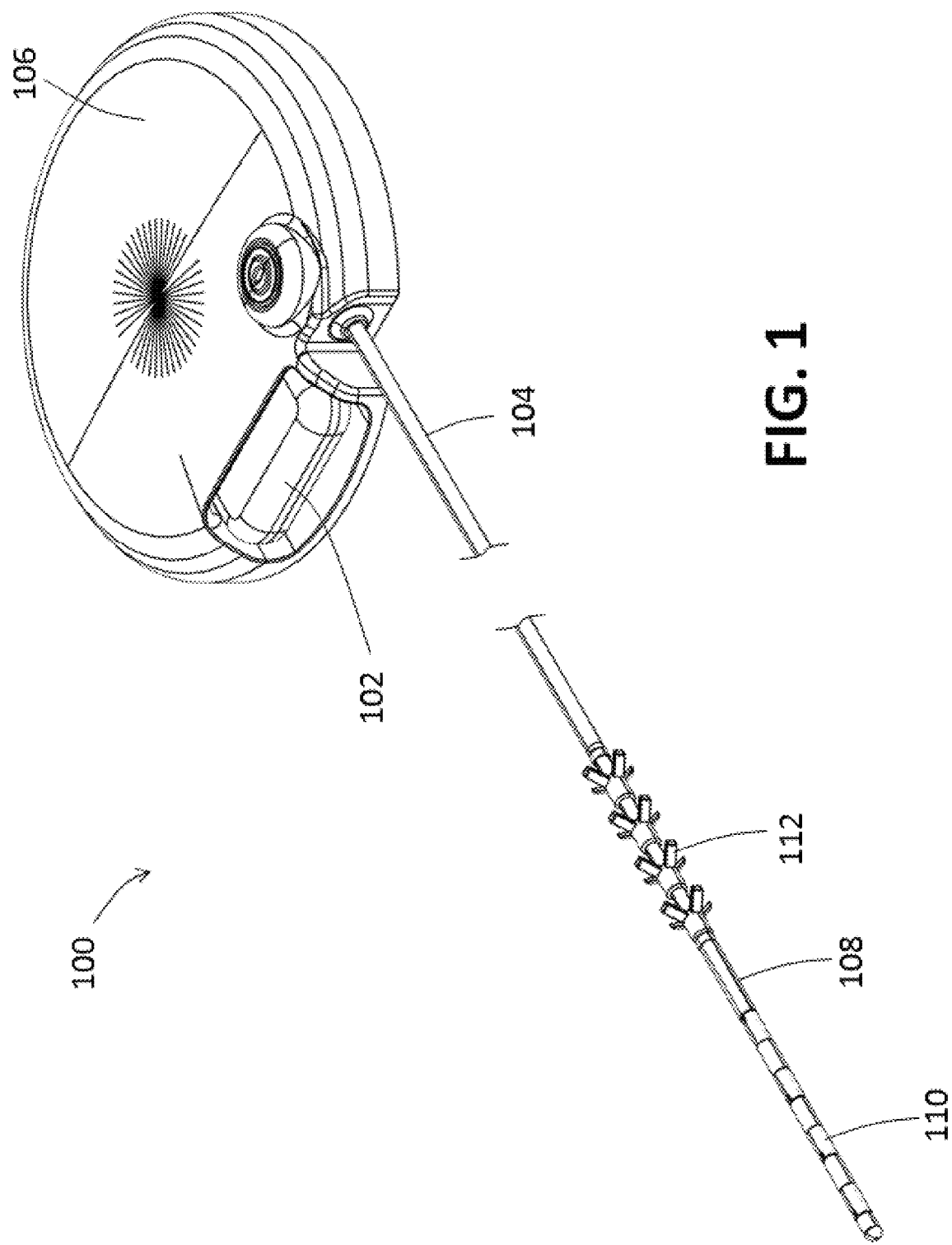
FIG. 1 is a perspective view depicting a neuromodulation system, in accordance with an embodiment of the disclosure.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Referring to FIG. 1, a perspective view of a neuromodulation system 100 is depicted in accordance with an embodiment of the disclosure. The neuromodulation system 100 can include a neurostimulator device 102, an implantable stimulation lead 104, and an adapter 106 configured to establish a compatible electrical connection between the neurostimulator device 102 and the implantable stimulation lead 104.

The implantable stimulation lead 104 can include a distal portion 108 including one or more stimulation electrodes 110 configured to transmit electrical pulses to a nerve, nerve tissue, or other target site within a patient. In one embodiment, the stimulation electrodes 110 can be configured as an array of four ring-shaped electrodes. In other embodiments, the stimulation lead 104 can include a greater or lesser number of electrodes, for example eight electrodes.

In some embodiments, the implantable stimulation lead 104 can include one or more barbs or tines 112 located in proximity to the distal portion 108. Over time, tissue surrounding the stimulation lead 104 can grow between the tines 112, thereby aiding in securing the stimulation lead 104 in a fixed position relative to the nerve or other target site within a patient. Although the stimulation lead 104 is depicted in FIG. 1 as having a generally elongate cylindrical body, the use of other types of leads, including paddle style leads is also contemplated.

With additional reference to FIGS. 2A-C, the implantable stimulation lead 104 can further include a proximal portion 114 including one or more electrical connectors 116 normally configured to be operably coupled to a neurostimulator device 102 or adapter 106. In one embodiment, the proximal portion 114 can include an array of four insulated ring-shaped connectors 116. In other embodiments, the stimulation lead 104 can include a greater or lesser number of connectors, for example eight connectors.

As depicted, the connectors 116 can be separated or spaced apart from one another at a fixed distance D, alternatively referred to as "pitch spacing" or "pitch." For example, in one embodiment, the plurality of connectors 116A-D can be spaced apart from one another at a pitch of approximately 0.170 inches (as depicted in FIG. 2A). In another embodiment, the plurality of connectors 116 A-D can be spaced apart from one another at a pitch of approximately 0.085 inches (as depicted in FIG. 2B). In yet another embodiment, the plurality of connectors 116 A-D can be spaced apart from one another at a pitch of approximately 2 mm (as depicted in FIG. 2C). Other pitch configurations are also contemplated. In addition to varying pitch configurations, stimulation leads 104 can differ in their outer diameter dimensions, general shape (e.g., blunt, tapered or rounded proximal end 115), as well as other physical characteristics.

In some embodiments, the proximal portion 114 can include a datum reference 117 configured to serve as a reference point for the spacing of the various connectors 116 or configured to serve as a physical stop when inserting the lead into a neurostimulator. For example, in one embodiment, the datum reference 117 can be located on the proximal end 115 of the stimulation electrode 110 (as depicted in FIGS. 2A and 2C), such that insertion of the lead 104 into the neurostimulator device until the datum reference 117 contacts a forward stop 119 thereby aligns the connections 116A-D of lead 104 with corresponding connector elements 138A-D of the neurostimulator device 102 and/or adapter 106. In another embodiment, the datum reference 117 can be located distally from the connectors 116A-D (as depicted in FIG. 2B), such that insertion of the lead 104 into the neurostimulator device until the datum reference 117 contacts an abutting surface 121 thereby aligns the connectors 116A-D of lead 104 with corresponding connector elements 138A-D of the neurostimulator device 102 and/or adapter 106.

In some embodiments, the neurostimulator device 102 and/or adapter 106 can include a set screw 132 configured to tighten against the proximal portion 114, thereby enabling the proximal portion 114 of the stimulation lead 104 to be secured in position relative to the neurostimulator device 102 and/or adapter 106. In some embodiments, the set screw 132 can be configured to contact at least one of the connectors 116D (as depicted in FIG. 2A), so as to be electrically active. In other embodiments, (as depicted in FIG. 2C) the set screw 132 can be electrically inactive, in that it does not contact any of the connectors 116A-D.

The neurostimulator device 102 can enclose electrical circuitry, such as a simulation engine, sensing circuits, controller, battery, and the like. Thus, the neurostimulator device 102 can be assembled as a complete unit and then subsequently mated with the stimulation lead 104 and adapter 106, thereby completing the neuromodulation system 100. In some cases, the neurostimulator device 102 can be utilized as a replacement for a previously implanted neurostimulator device which has reached or is nearing the end of its serviceable life (e.g., the previously implanted neurostimulator device may have a primary cell or battery that is near exhaustion) or is otherwise contemplated being replaced.

Figure 4A:
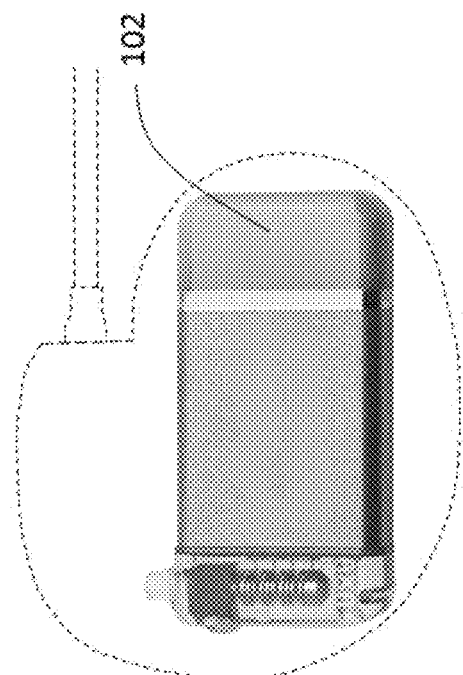
FIG. 4A is a plan view depicting a replacement neurostimulator device, in accordance with an embodiment of the disclosure.
Figure 4B:
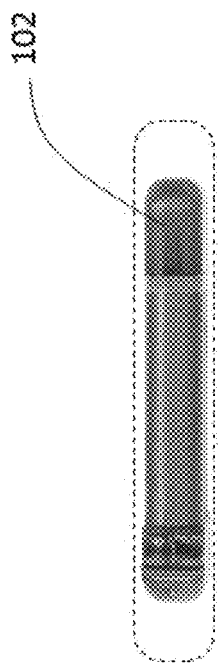
FIG. 4B is a profile view of the neurostimulator device of FIG. 4A.
Figure 3A:
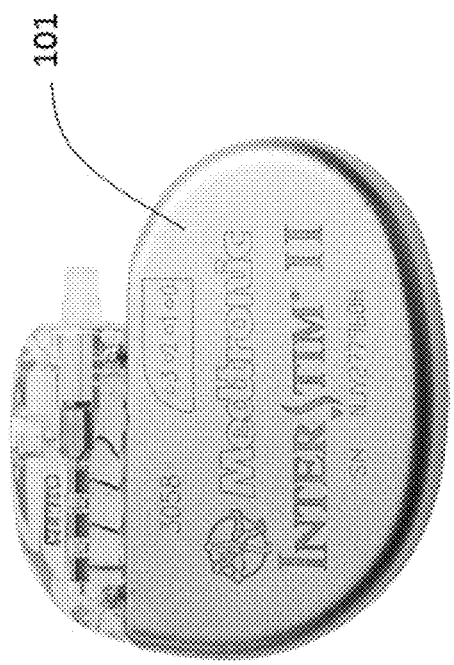
FIG. 3A is a plan view depicting an Interstim® II sacral neuromodulation neurostimulator device.
Figure 3B:
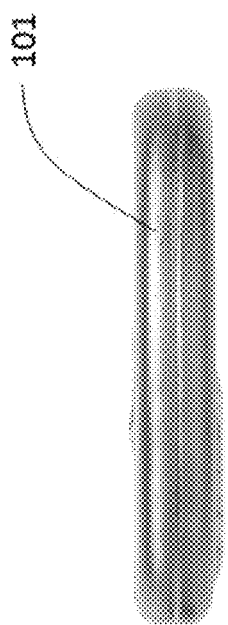
FIG. 3B is a profile view of the neurostimulator device of FIG. 3A.

With reference to FIGS. 3A-4B, where the neurostimulator device is serving as a replacement device 102, the replacement device 102 may be more compact and/or have a different shape than the previously implanted device 101. For example, FIGS. 3A-B depict the Interstim® II sacral neuromodulation neurostimulator device 101, manufactured and sold by Medtronic. FIGS. 4A-B depict an example of a replacement neurostimulator device 102, which can differ both in shape and size from the Interstim® device 101. Other differences may include the orientation or angle at which the stimulation lead extend from the devices 101, 102, as well as the connector 116 pitch spacing of the stimulation leads designed to be used with the different devices 101, 102. For example, a previously implanted stimulation lead may have an electrical connector with a pitch spacing of about 0.170 inches, while the replacement neurostimulator device 102 may be configured to receive a stimulation lead having connectors 116 with a pitch spacing of about 0.085 inches or about 2 mm. Accordingly, without modification, a replacement device 102 may be incompatible with a previously implanted stimulation lead 104.

Figure 5A:
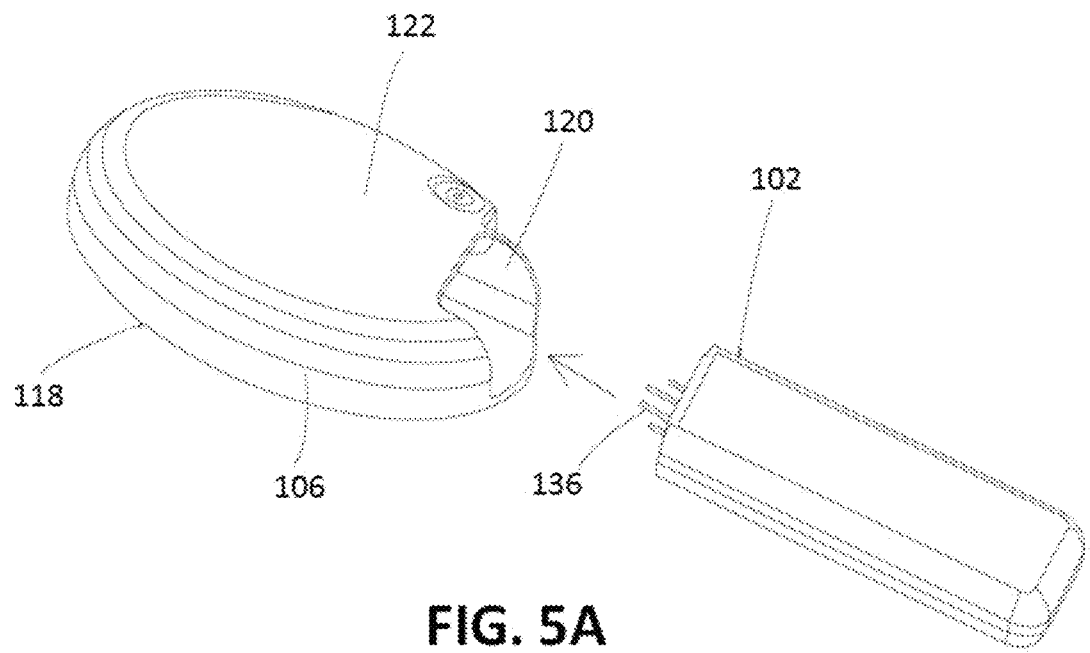
FIG. 5A is a perspective view depicting a first neurostimulator device and adapter, in accordance with an embodiment of the disclosure.
Figure 5B:
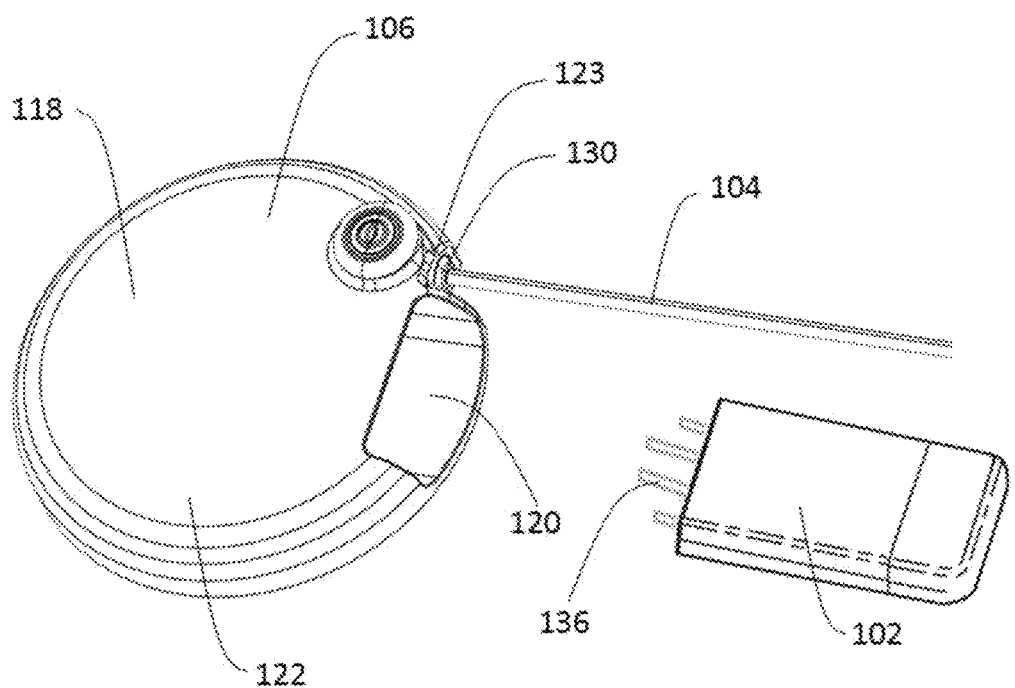
FIG. 5B is a perspective view depicting a second neurostimulator device and adapter, in accordance with an embodiment of the disclosure.

With reference to FIGS. 5A-B, to address this concern, an adapter 106 can be configured to enable an electrically compatible connection between a previously implanted stimulation lead 104 and a replacement neurostimulator device 102. The adapter 106 can include a housing 118 defining a first cavity 120 shaped and sized to receive at least a portion of the replacement neurostimulator device 102 therein. While the neurostimulator device 102 is depicted in FIGS. 5A-B as having a rectangular shape, it will be appreciated that other shapes and configurations are also possible. Further, as depicted in FIGS. 5A-B, the replacement neurostimulator device 102 can be modified to remove a header portion of the device (depicted in FIGS. 2B-C), thereby enabling ease in electrical connection between the replacement neurostimulator device 102 and one or more electrical conductors within the adapter 106.

In some embodiments, the adapter 106 can have a shape and size, and/or be constructed of a material that is specific to the particular location within the patient that the system 100 is to be implanted. For example, where the neurostimulator device 102 serves as a replacement for a previously implanted neurostimulator device, an exterior 122 of the adapter 106 can be shaped and sized to generally mimic the shape and size of the previously implanted neurostimulator device, thereby minimizing any perceived differences between the previously implanted device and the adapter 106. Accordingly, in some embodiments, the adapter 106 is configured to fit within an established pocket or cavity within the patient. For example, in one embodiment, the exterior 122 of the housing 118 can have a round, disc-like shape having a notch 123 in the otherwise round periphery where an opening to a second cavity 130 is located. In an embodiment, the notch 123 may enable the stimulation lead 104 to begin an arc as the lead 104 extends away from the second cavity 130, so as to coil any excess length of lead 104 for strain relief purposes.

In some embodiments, the adapter 106 can be constructed of a material, such as a biocompatible polymer, configured to offer protection to the neurostimulator device 102, while also providing a suitable interface to subcutaneous tissues at the particular area of implementation. Furthermore, while the adapter 106 can be constructed of a polymer, such as polysulfone, or polyether ether ketone (PEEK) and the like, it will be appreciated that other biocompatible materials can be used.

Figure 6:
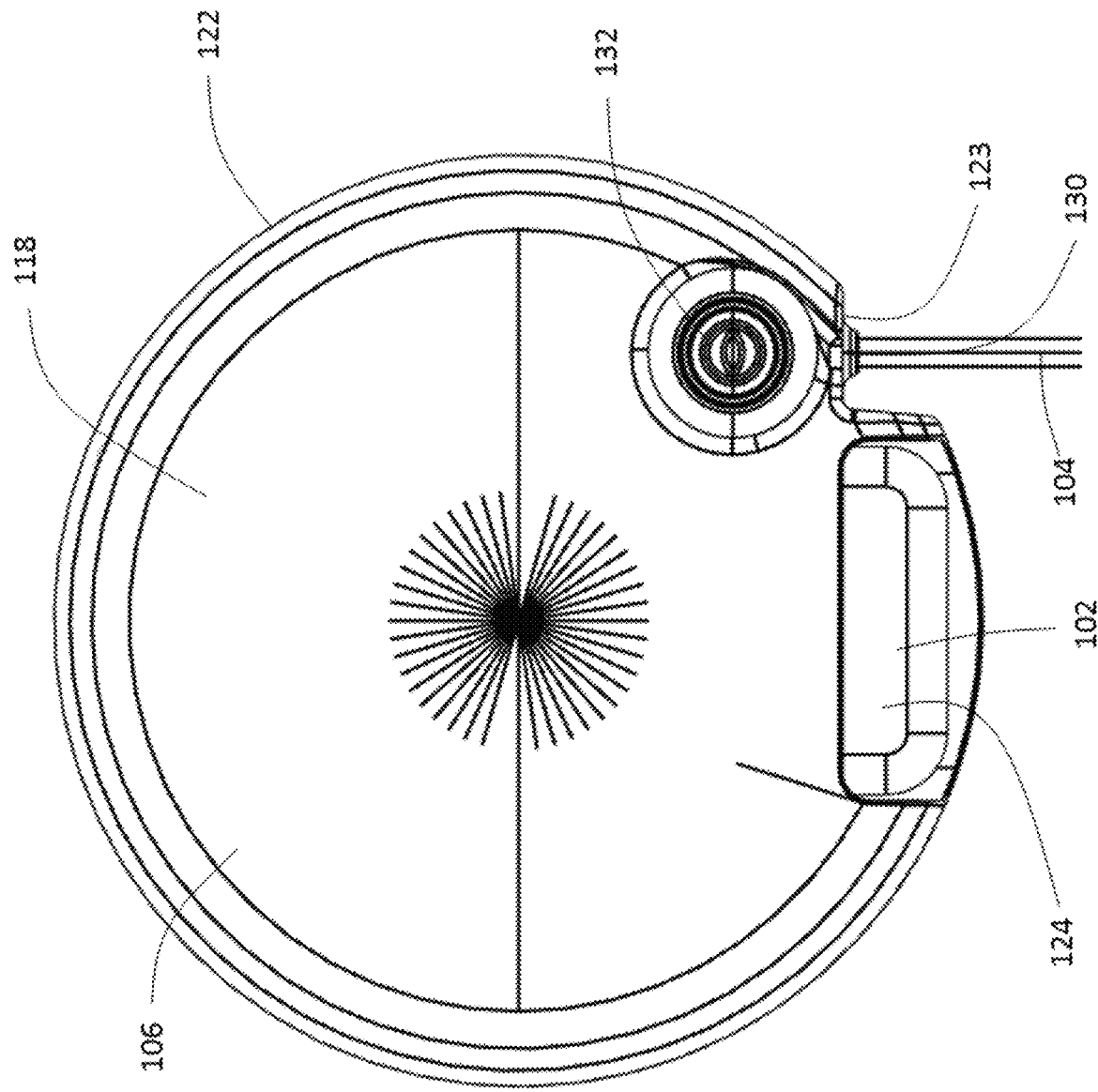
FIG. 6 is a close-up, partial, top plan view depicting a neuromodulation system, in accordance with an embodiment of the disclosure.
Figure 7:
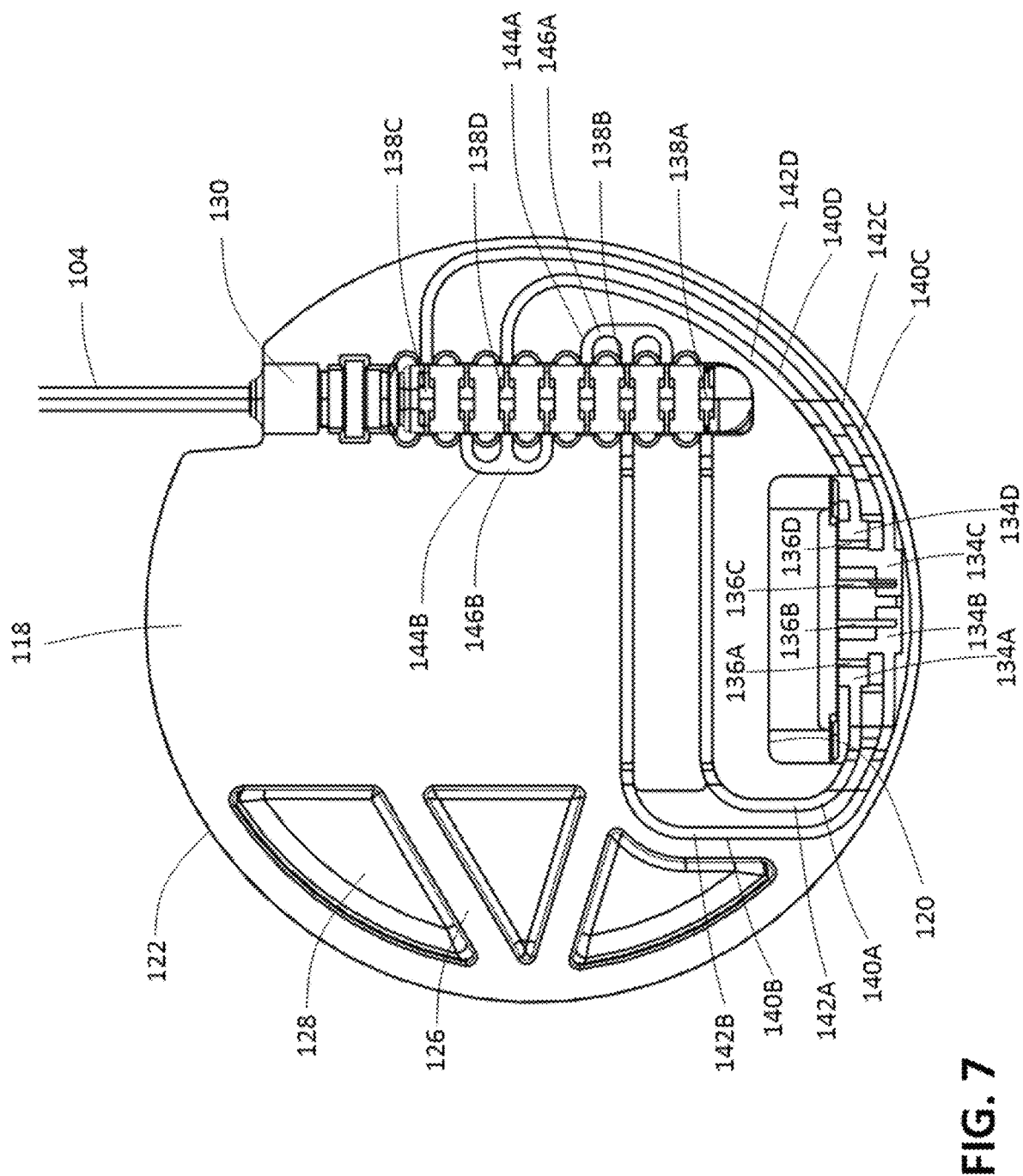
FIG. 7 is a close-up, partial, bottom plan view depicting the neuromodulation system of FIG. 3.

With additional reference to FIGS. 6 and 7, where the adapter 106 is sized larger than the neurostimulator device 102 to fill a preestablished pocket or cavity within the patient, the adapter 106 can include one or more webs 126 (depicted in FIG. 7) configured to add structural support to one or more voids 128 defined within the housing 118. In some embodiments, a medical adhesive or similar biocompatible material can be applied to fill in the voids that are present between the neurostimulator device 102 and first cavity 120 of the adapter 106.

While the neurostimulator device 102 is located in the first cavity 120 of the adapter 106, it can be seen in the example shown that a portion of the end of the neurostimulator device 102 is not covered by the adapter 106, so as to be exposed through an aperture 124 defined in the exterior surface 122 of the adapter 106. In some embodiments, the exposed portion of the neurostimulator device 102 can remain uncovered by medical adhesive, so that if the neurostimulator device 102 is configured for recharging from an external device, the portion of the neurostimulator device 102 containing the induction coil can be exposed for minimum interference while recharging. Alternatively, in some embodiments, the exposed portion of the neurostimulator device 102 can act as a node for stimulation and sensing circuits, such as for unipolar stimulation.

Although the aperture 124 is depicted at one end of the neurostimulator device 102 other positions of the aperture 124, such as in the center of the adapter 106, are also contemplated. Additionally, in some embodiments, more than a single aperture 124 can be defined in the housing 118 of the adapter 106. For example, in one embodiment, an aperture 124 may be arranged and configured to facilitate an unimpeded telemetry link between the device 102 and an external programmer.

The housing 118 can further define a second cavity 130 shaped and sized to receive the proximal portion 114 of the implantable stimulation lead 104. As depicted in FIG. 6, in some embodiments, the housing 118 can include a set screw 132 configured to tighten against the proximal portion 114 received within the second cavity 130, thereby enabling the proximal portion 114 of the stimulation lead 104 to be secured in position relative to the housing 118. Other mechanisms for locking or securing the stimulation lead 104 to the adapter 106 are also contemplated. In other embodiments, the proximal portion 114 of the lead 104 can be coupled to an extension, with the extension being coupled to the second cavity 130 of the housing 118.

With reference to FIG. 7, a plurality of electrical conductors 134A-D can be positioned within the first cavity 120 for contact with a plurality of electrical terminals 136A-D emanating from the neurostimulator device 102 (depicted in FIGS. 5A-B as feedthrough pins 136 extending from the neurostimulator device 102). For example, in one embodiment, the adapter 106 can include four electrical conductors in the form of conductive pads 134A-D; however, a greater or lesser number of pads is also contemplated. Alternatively, other forms of contact between the electrical terminals 136 and the electrical conductors 134A-D, such as frictional engagement via a spring-loaded connector, or cross welding between electrical conductors 134A-D and terminals 136A-D are also contemplated.

The plurality of electrical conductors 134A-D can be in electrical communication with a corresponding plurality of connector elements 138A-D configured to contact the electrical connectors 116 of the stimulation lead 104 received within the second cavity 130. For example, in one embodiment, the plurality of electrical conductors 134A-D can be electrically coupled to the corresponding plurality of connector elements 138A-D by way of a plurality of wires 140A-D or other electrical conduits, which in one embodiment can be routed within one or more channels 142A-D defined within the housing 118.

In one embodiment, one or more bridging channels 144A-B can be defined by the housing 118 for the purpose of containing one or more bridging connectors 146A-B that bridges multiple electrical conductors 140A-D in parallel. Bridging connectors 146A-B can be utilized, for example, where the neurostimulator device 102 has fewer electrical contacts 136 than the stimulation lead 104 has electrical connectors 116. In some embodiments, the housing 118 can define a forward stop 147 and/or abutting surface 149 configured to interact with a datum reference 119 of the stimulation lead 104, to ensure that the electrical connectors of the stimulation lead 104 are appropriately positioned with respect to the connector elements 138.

Once the electrical connections have been established among the various components, a medical adhesive or other similar filler material can be applied to fill both the first cavity 120 and the second cavity 130 to encapsulate the components installed therein. Additionally, the filler material can be applied within the channels 142A-D to encapsulate the conductors 140A-D. The filler material can be applied to completely fill the cavities 120, 130 and channels 142 to electrically isolate the various components and create a flush exterior surface 122 of the adapter 106.

While the example shown has a round, disc-like shape, the adapter 106 can be in the form of other shapes and/or sizes while providing both a first cavity 124 receiving the neurostimulator device 102 and a second cavity 130 receiving a portion of the stimulation lead 104. Furthermore, the orientation of the first cavity 120 and the second cavity 130 can vary from the parallel configuration shown, such as where the longitudinal dimension of each cavity 120/130 forms an angle with respect to each other, including a generally perpendicular orientation. Thus, the round, disc-like shape is shown only for purposes of demonstrating one exemplary embodiment.

Figure 8:
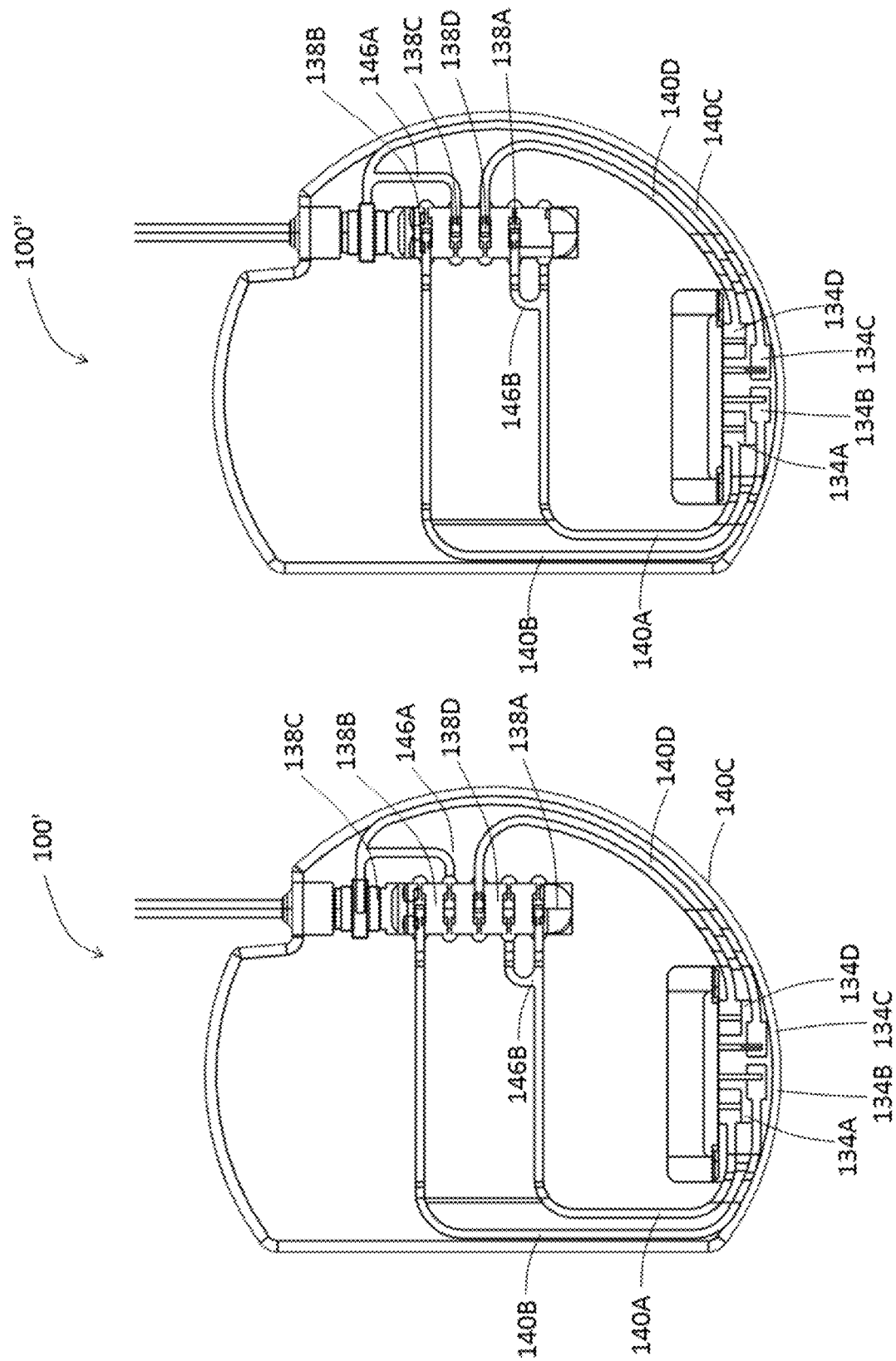
FIG. 8A is a close-up, partial, bottom plan view depicting the neuromodulation system in accordance with a second embodiment of the disclosure.
FIG. 8B is a close-up, partial, bottom plan view depicting the neuromodulation system in accordance with a third embodiment of the disclosure.

For example, with reference to FIGS. 8A-B, neural stimulation systems 100',100" having a generally "D" shaped adapter are depicted in accordance with an embodiment of the disclosure. With continued reference to FIGS. 8A-B, the plurality of electrical conductors 134A-D can be in electrical communication with a corresponding plurality of connector elements 138A-D configured to contact the electrical connectors 116 of the stimulation lead 104 received within the second cavity 130. For example, in one embodiment, the plurality of electrical conductors 134A-D can be electrically coupled to the corresponding plurality of connector elements 138A-D by way of a plurality of wires 140A-D or other electrical conduits. One or more bridging connectors 146A-B can be utilized, for example, where the neurostimulator device 102 has fewer electrical contacts 136 than the stimulation lead 104 has electrical connectors 116. Other aspects of the neurostimulator systems 100',100" can be like that of the previously disclosed embodiments.

Accordingly, in some embodiments, the adapter 106 can be configured to establish a compatible electrical connection between a neurostimulator device 102 (which may be a replacement for a previously implanted neurostimulator device) and an implantable stimulation lead 104 (which may have been previously implanted into the patient). For example, in one embodiment, the neuromodulation adapter 106 can be configured to electrically connect a previously implanted stimulation lead 104 having a plurality of electrical connectors 116 spaced apart from one another at a first pitch with a replacement neurostimulator device 102 generally configured to mate with a stimulation lead 104 having a plurality of electrical connectors 116 spaced apart from one another at a second pitch. In embodiments, the first pitch can be approximately 0.170 inches, and the second pitch can be approximately 0.085 inches or approximately 2 mm (as depicted in FIG. 8A). In another embodiment, the neuromodulation adapter 106 can be configured to electrically connect a previously implanted stimulation lead 104 having a plurality of electrical connectors 116 spaced apart from one another at a first pitch of approximately 0.085 inches with a replacement neurostimulator device 102 generally configured to mate with a stimulation lead 104 having a plurality of electrical connectors 116 spaced apart from one another in a second pitch of approximately 2 mm, or vice versa (as depicted in FIG. 8B).

Figure 9:
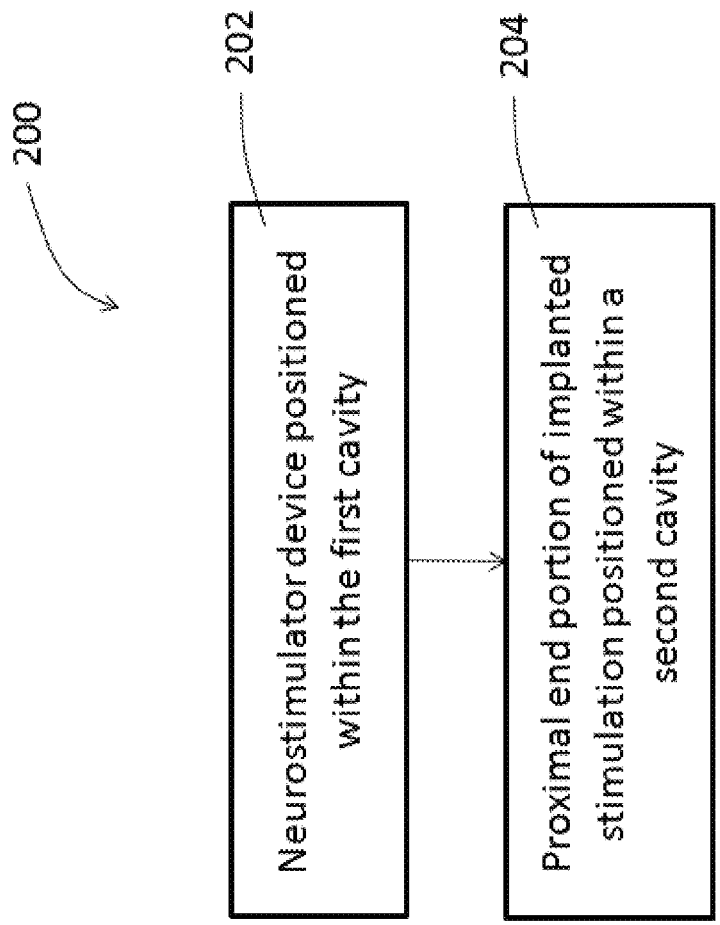
FIG. 9 is a flowchart depicting a method of electrically coupling a stimulation lead with a neurostimulator device, in accordance with an embodiment of the disclosure.
Figure 11A:
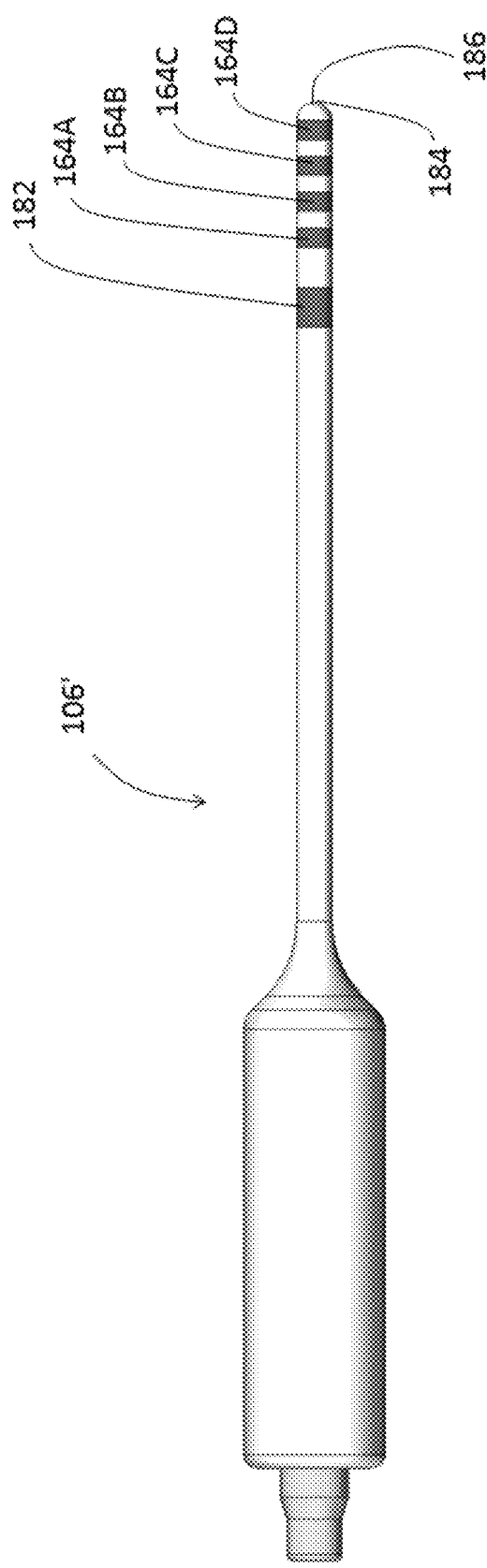
FIG. 11A is a profile view depicting a neuromodulation adapter, in accordance with an embodiment of the disclosure.
Figure 11B:
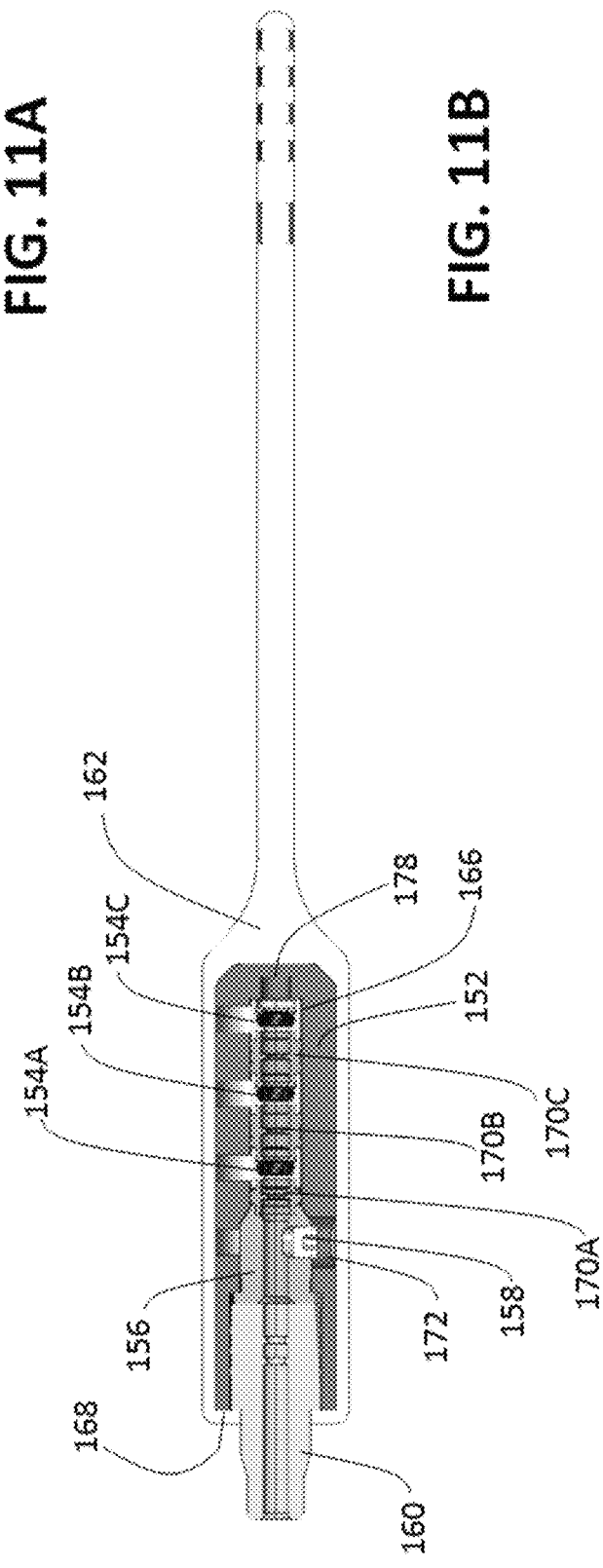
FIG. 11B is a cross-sectional view depicting the neuromodulation adapter of FIG. 11A.

With reference to FIG. 9, a method 200 of electrically coupling a previously implanted stimulation lead 104 with a replacement neurostimulator device 102 is depicted in accordance with an embodiment of the disclosure. At 202, at least a portion of a replacement neurostimulator device 102 can be positioned within the first cavity 120 defined by the housing 118 of the neuromodulation adapter 106. The housing 118 can include a plurality of electrical conductors 134A-D configured to contact the electrical terminals 136 of the neurostimulator device 102.

At 204, a proximal end portion 114 of a previously implanted stimulation lead 104 can be positioned within a second cavity 130 defined by the housing 118 of the neuromodulation adapter 106. The housing can include a plurality of connector elements 138 configured to contact the electrical connectors 116 of the previously implanted stimulation lead 104. The plurality of electrical conductors 134 can be electrically coupled to the plurality of connector elements 138, thereby enabling an electrical compatible connection between the previously implanted stimulation lead 104 and a replacement neurostimulator device 102.

With reference to FIGS. 10A-11B, in another embodiment, the adapter 106' can be configured as an extension of the implantable stimulation lead 104, thereby providing an electrical coupling between an otherwise incompatible stimulation lead 104 and neurostimulator device 102. For example, in one embodiment, the adapter 106' can include a proximal portion 148 configured to be received within a stimulation lead port of a neurostimulator device 102, and a distal portion 150 configured to receive a proximal portion of a stimulation lead 104.

As depicted in FIG. 10B, in one embodiment, the adapter 106' can include a chassis 152, a plurality of connector elements 154A-D, a set screw block 156, a set screw 158, a rear seal 160, a boot 162, and a plurality of electrical conductors 164A-D. With additional reference to FIG. 11A-B, in one embodiment, the chassis 152 can be constructed of a rigid or semi-rigid biocompatible, nonconductive material, such as PEEK, or other material that bonds well to an over-molded liquid silicone rubber material. In one embodiment, the chassis 152 can define a blind bore 166 extending proximally from a distal surface 168, shaped and sized to receive the plurality of conductor elements 154A-C, set screw block 156, and at least a portion of the rear seal 160.

In one embodiment, the connector elements 154A-C can form complete circular structures, examples of which include Bal Seal® canted coil connectors. The connector elements 154A-C can be separated from one another by insulative spacers 170A-C, such that the connector elements 154A-C and insulative spacers 170A-C are interleaved along a longitudinal axis of the chassis 152. The insulative seals 170A-C can provide wiper seals, and can be constructed of a biocompatible compliant material such as silicone. In some embodiments, the insulative seals 170A-C can be compressible to some degree along the longitudinal axis, so as to create a tight fit between adjacent connector elements 154.

In one embodiment, the chassis 152 can further include a set screw bore 172, thereby enabling threaded insertion of the set screw 158 into the set screw block 156. In some embodiments, the set screw block 156 can be axially aligned with the connector elements 154A-C, such that the electrically active set screw 158 contacts an electrical connector of a stimulation lead 104 inserted into the distal portion 150 of the adapter 106'.

Although the adapter 106' is depicted as having three connector elements 154A-C plus active set screw 158, and three insulative seals 170A-C, other quantities of connector elements and insulative seals are also contemplated. For example, in one embodiment, the adapter 106' can include four connector elements 154A-C (with an electrically inactive set screw 158). In either case, the set screw 158 can be configured to tighten against a portion of an stimulation lead 104 received within the distal portion 150 of the adapter 106', thereby enabling the stimulation lead 104 to be secured in position relative to the adapter 106'. In some embodiments, the blind bore 166, set screw block 156 and/or rear seal 160 can define a forward stop 178 and/or abutting surface 180 configured to interact with a datum reference of the stimulation lead 104, to ensure that the electrical connectors of the stimulation lead 104 are appropriately positioned with respect to the connector elements 154 and/or set screw 158.

During assembly, the connector elements 154A-C, insulative spacers 170A-C, and set screw block 156 can be sequentially inserted into the blind bore 166 of the chassis 152. In one embodiment, the set screw block 156 can define a flat or keyed surface 174 depicted in FIG. 10B, configured to matingly engage with a corresponding flat or keyed surface defined by the blind bore 166 of the chassis 152, thereby inhibiting rotation of the set screw block 156 relative to the chassis 152 during operation. The rear seal 160, can be inserted into the blind bore 166, thereby providing a distal surface 168 seal of the chassis 152. In some embodiments, the rear seal 160 can include one or more wipers 176 configured aid in sealing the connector elements 154, insulative spacers 170, and set screw block 156 within the chassis 152. Thereafter, the boot 162 can be applied to the exterior of the chassis 152. For example, in one embodiment, the boot 162, which can be constructed of liquid silicone rubber, can be over-molded over the chassis 152 and a portion of the rear seal 160 extending therefrom.

The plurality of electrical conductors 164A-D can be positioned on a proximal portion 148 of the boot 162. For example, in one embodiment, the adapter 106' can include four electrical conductors 164A-D configured to electrically couple to the corresponding electrical terminals of a neurostimulator device 102. For example, in some embodiments, the proximal portion 148 of the adapter 106' can be configured to be received within a header portion of the neurostimulator device 102 (as depicted in FIGS. 2B-C). The electrical conductors 164A-D can be in electrical communication with the connector elements 154A/C and/or set screw block 156 via one or more wires, cables or other connecting elements. In some embodiments, a portion of the boot 162 located between the electrical conductors 164 and the connector elements 154 can be flexible, so as to enable bending of the adapter 106' to aid in ideal positioning of the neurostimulator device 102 relative to the stimulation lead 104 within the body of a patient.

In some embodiments, the proximal portion 148 can further include a set screw ring 182 configured to withstand the compressive force of a set screw of the neurostimulator device 102. In some embodiments, the proximal portion 148 can include a datum reference 184 configured to serve as a reference point for the spacing of the various connectors electrical conductors 164. In some embodiments, the data reference 184 can be positioned at a proximal end 186 of the adapter 106'. In other embodiments, the datum reference 184 can be positioned distally from the electrical conductors 164 (not depicted).

Accordingly, in some embodiments, the adapter 106' can be configured to establish a compatible electrical connection between a neurostimulator device 102 (which may be a replacement for a previously implanted neurostimulator device) and an implantable stimulation lead 104 (which may have been previously implanted into the patient). For example, in one embodiment, the neuromodulation adapter 106 can be configured to electrically connect a previously implanted stimulation lead 104 having a plurality of electrical connectors 116 spaced apart from one another at a first pitch with a replacement neurostimulator device 102 generally configured to mate with a stimulation lead 104 having a plurality of electrical connectors 116 spaced apart from one another at a second pitch. In embodiments, the first pitch can be approximately 0.170 inches, and the second pitch can be approximately 0.085 inches or approximately 2 mm. In another embodiment, the neuromodulation adapter 106 can be configured to electrically connect a previously implanted stimulation lead 104 having a plurality of electrical connectors 116 spaced apart from one another at a first pitch of approximately 0.085 inches with a replacement neurostimulator device 102 generally configured to mate with a stimulation lead 104 having a plurality of electrical connectors 116 spaced apart from one another in a second pitch of approximately 2 mm, or vice versa.

Figure 12:
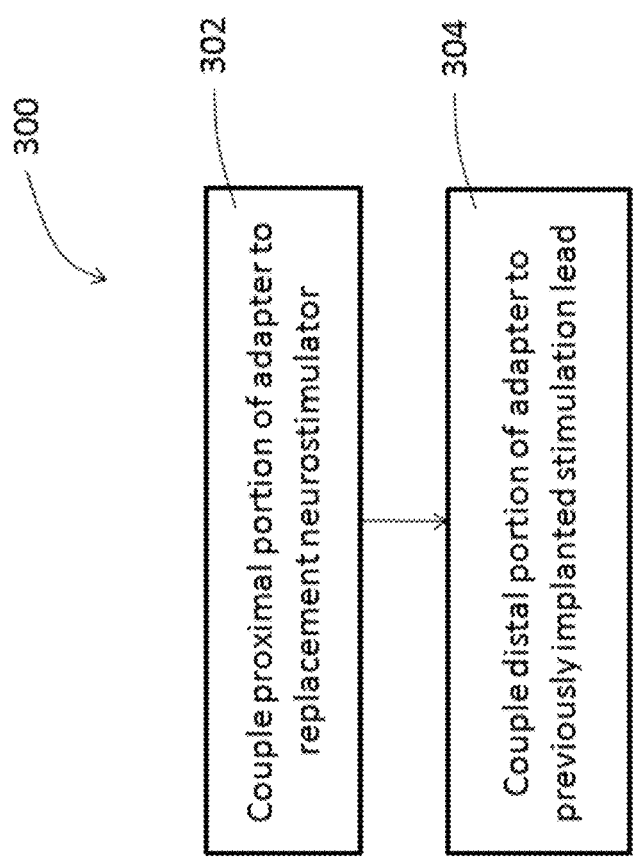
FIG. 12 is a flowchart depicting a method of electrically coupling a stimulation lead with a neurostimulator device, in accordance with an embodiment of the disclosure.

With reference to FIG. 12, a method 300 of electrically coupling a previously implanted stimulation lead 104 with a replacement neurostimulator device 102 is depicted in accordance with an embodiment of the disclosure. At 302, a proximal portion 148 of a neuromodulation adapter 106' including a plurality of electrical conductors 164 spaced apart at a first pitch spacing is operably coupled to a corresponding plurality of electrical terminals of a replacement neurostimulator device 102.

At 304, a distal portion 150 of the neuromodulation adapter 106' including a plurality of conductor elements 154 and electrically active set screw 158 spaced apart at a second pitch spacing, are operably coupled to a corresponding plurality of electrical connectors of a previously implanted stimulation lead 104, thereby enabling an electrical compatible connection between the previously implanted stimulation lead 104 and a replacement neurostimulator device 102.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A neuromodulation adapter configured to provide an electrical coupling between an otherwise incompatible stimulation lead and neurostimulator device, the neuromodulation adapter comprising:
   a proximal portion including a plurality of electrical conductors spaced apart at a first pitch spacing and configured to electrically engage with a corresponding plurality of electrical terminals of a neurostimulator device; and
   a distal portion including plurality of conductor elements and an electrically active set screw, the plurality of conductor elements and electrically active set screw spaced apart at a second pitch spacing and configured to electrically engage with a corresponding plurality of electrical connectors of a stimulation lead, wherein the first pitch spacing is different from the second pitch spacing,
   wherein the proximal portion includes a datum reference configured to serve as a reference point for spacing of the plurality of electrical conductors relative to a corresponding plurality of electrical terminals of a neurostimulator device.

2. The neuromodulation adapter of claim 1, wherein the distal portion includes at least one of a forward stop or abutting surface configured to serve as a reference point for spacing of the plurality of conductor elements relative to a corresponding plurality of electrical connectors of a stimulation lead.

3. The neuromodulation adapter of claim 1, wherein the first pitch spacing has a pitch of at least one of about 0.085 inches or about 2 mm.

4. The neuromodulation adapter of claim 1, wherein the second pitch spacing has a pitch of about 0.170 inches.

5. The neuromodulation adapter of claim 1, further comprising a flexible portion located between the proximal portion and the distal portion, configured to enable bending of the neuromodulation adapter to aid in an ideal positioning of a neurostimulator device relative to a stimulation lead within a body of a patient.

6. A neuromodulation adapter configured to provide an electrical coupling between a stimulation lead having a pitch spacing of about 0.170 inches and neurostimulator device having a pitch spacing at least one of about 0.085 inches or about 2 mm, the neuromodulation adapter comprising:
   a proximal portion including a plurality of electrical conductors spaced apart at a first pitch spacing at least one of about 0.085 inches or about 2 mm and configured to electrically engage with a corresponding plurality of electrical terminals of a neurostimulator device, wherein the proximal portion further includes a datum reference configured to serve as a reference point for spacing of the plurality of electrical conductors relative to a corresponding plurality of electrical terminals of a neurostimulator device; and
   a distal portion including plurality of conductor elements and an electrically active set screw, the plurality of output conductors and electrically active set screw spaced apart at a second pitch spacing of about 0.170 inches and configured to electrically engage with a corresponding plurality of electrical connectors of a stimulation lead, wherein the distal portion further includes at least one of a forward stop or abutting surface configured to serve as a reference point for spacing of the plurality of conductor elements relative to a corresponding plurality of electrical connectors of a stimulation lead.

7. A neuromodulation adapter comprising:
   a housing defining a first cavity shaped and sized to receive at least a portion of an implantable neurostimulator device therein, and second cavity shaped and sized to receive a proximal end portion of a stimulation lead, and
   a plurality of electrical conductors configured to contact a plurality of electrical terminals of the implantable neurostimulator device received within the first cavity, the plurality of electrical conductors in electrical communication with a corresponding plurality of connector elements configured to contact a plurality of electrical connectors of the proximal end of the stimulation lead received within the second cavity, thereby enabling an electrically compatible connection between a previously implanted stimulation lead and a replacement implantable neurostimulator device,
   wherein the second cavity includes a forward stop configured to serve as a reference point for spacing of the plurality of connector elements relative to a corresponding plurality of electrical connectors of the stimulation lead.

8. The neuromodulation adapter of claim 7, wherein the plurality of electrical conductors are electrically connected to the plurality of connector elements via a corresponding plurality of wires routed within channels defined by the housing.

9. The neuromodulation adapter of claim 7, wherein an exterior of the housing has a round disc-like shape.

10. The neuromodulation adapter of claim 7, wherein an exterior of the housing has a generally "D" shaped configuration.

11. The neuromodulation adapter of claim 7, wherein an exterior of the housing is shaped and sized to generally mimic the shape and size of a previously implanted implantable neurostimulator device.

12. The neuromodulation adapter of claim 7, wherein the plurality of connector elements configured to contact the plurality of electrical connectors of a proximal end of a stimulation lead received within the second cavity are spaced apart from one another at a pitch of about 0.170 inches.

13. The neuromodulation adapter of claim 9, further comprising a set screw configured to enable the proximal end of the stimulation lead received within the second cavity to be secured in position relative to the housing.

14. The neuromodulation adapter of claim 7, wherein an exterior of the housing includes an aperture configured to expose at least a portion of the implantable neurostimulator device received within the first cavity.

\* \* \* \* \*